US012697288B2

(12) United States Patent
Ishii et al.

(10) Patent No.: US 12,697,288 B2
(45) Date of Patent: Aug. 4, 2026

(54) COMPOSITION FOR ORAL CAVITY

(71) Applicant: SUNSTAR INC., Osaka (JP)

(72) Inventors: Shuhei Ishii, Osaka (JP); Taku Ideue, Osaka (JP)

(73) Assignee: SUNSTAR INC., Osaka (JP)

( * ) Notice: Subject to any disclaimer, the term of this patent is extended or adjusted under 35 U.S.C. 154(b) by 0 days.

(21) Appl. No.: 17/236,649

(22) Filed: Apr. 21, 2021

(65) Prior Publication Data

US 2021/0244636 A1     Aug. 12, 2021

Related U.S. Application Data

(63) Continuation-in-part of application No. PCT/JP2019/041444, filed on Oct. 23, 2019.

(30) Foreign Application Priority Data

| Oct. 24, 2018 | (JP) | 2018-199776 |
| Oct. 24, 2018 | (JP) | 2018-199779 |
| Oct. 24, 2018 | (JP) | 2018-199781 |
| Oct. 24, 2018 | (JP) | 2018-199784 |

(51) Int. Cl.
| *A61K 8/34* | (2006.01) |
| *A61K 8/31* | (2006.01) |
| *A61K 8/37* | (2006.01) |
| *A61K 8/92* | (2006.01) |
| *A61Q 11/00* | (2006.01) |

(52) U.S. Cl.
CPC ............... *A61K 8/345* (2013.01); *A61K 8/31* (2013.01); *A61K 8/375* (2013.01); *A61K 8/922* (2013.01); *A61Q 11/00* (2013.01)

(58) Field of Classification Search
CPC . A61K 8/39; A61K 8/31; A61K 8/375; A61K 8/922; A61K 8/86; A61K 8/604; A61K 8/345; A61K 2800/31; A61Q 11/00
See application file for complete search history.

(56) References Cited

U.S. PATENT DOCUMENTS

| 4,512,968 | A | 4/1985 | Komiyama et al. | |
| 6,475,470 | B1 | 11/2002 | Kayane et al. | |
| 2004/0037790 | A1 * | 2/2004 | Watanabe .............. | A61K 36/65 |
| | | | | 424/769 |
| 2004/0132815 | A1 | 7/2004 | Kimoto | |
| 2008/0102042 | A1 | 5/2008 | Shimada et al. | |
| 2011/0205778 | A1 | 8/2011 | Nagatomo | |

FOREIGN PATENT DOCUMENTS

| CA | 2575693 | A1 * | 3/2006 | |
| CN | 1735397 | A * | 2/2006 | .............. A61K 8/26 |
| JP | H05-331031 | A | 12/1993 | |
| JP | 2001-039842 | A | 2/2001 | |
| JP | 2001-072559 | A | 3/2001 | |
| JP | 2001-206830 | A | 7/2001 | |
| JP | 2001-335447 | A | 12/2001 | |
| JP | 2002114657 | A * | 4/2002 | |
| JP | 2006-241113 | A | 9/2006 | |
| JP | 2006-312590 | A | 11/2006 | |
| JP | 3977553 | * | 9/2007 | |
| JP | 2008081424 | A * | 4/2008 | |
| JP | 2009-095253 | A | 5/2009 | |
| JP | 2010-189358 | A | 9/2010 | |
| JP | 2011-126819 | A | 6/2011 | |
| JP | 2011-236144 | A | 11/2011 | |
| JP | 2013-224318 | A | 10/2013 | |
| JP | 2014-189550 | A | 10/2014 | |
| JP | 2016-086795 | A | 5/2016 | |
| KR | 2003-0092073 | A | 12/2003 | |
| KR | 10-1436923 | B1 | 9/2014 | |
| WO | WO 2006/046690 | A1 | 5/2006 | |
| WO | WO 2018/145966 | A1 | 8/2018 | |

OTHER PUBLICATIONS

Aug. 30, 2022, European Search Report issued for corresponding EP Application No. 19876983.8.
Oct. 29, 2019, Japanese Office Action issued for related JP application No. 2018-199776.
Oct. 29, 2019, Japanese Office Action issued for related JP application No. 2018-199779.
Sun Drug, Pyorrhoea Alveolaris Dental Ointment, Daiichi Sankyo Healthcare, Japan, Retrieved from: https://portal.mintel.com, Nov. 2015.
Jun. 9, 2020, Japanese Office Action issued for related JP application No. 2018-199776.
Akbari et al., Emulsion types, stability mechanisms and rheology: A review, International Journal of Innovative Research and Scientific Studies, Sep. 21, 2018, pp. 14-21.
Wang et al., Emulsion and its application in the food field: An update review, eFood, 2023, pp. 1-18.

* cited by examiner

*Primary Examiner* — Lezah Roberts
(74) *Attorney, Agent, or Firm* — Paratus Law Group, PLLC

(57) ABSTRACT

Provided is an oral composition that has excellent stability over time although a hydrocarbon oil is contained therein. Specifically provided is an oral composition comprising a hydrocarbon oil, a polyhydric alcohol, and a surfactant, the oral composition comprising (i) glycerol, and a polyglycerol fatty acid ester and/or an alkyl glucoside, (ii) propanediol, and a polyoxyethylene hardened castor oil and/or a polyoxyethylene hardened castor oil fatty acid ester, (iii) butylene glycol, and a polyoxyethylene alkyl ether and/or a polyoxyethylene hardened castor oil fatty acid ester, or (iv) polyethylene glycol and a polyoxyethylene hardened castor oil fatty acid ester.

20 Claims, No Drawings

COMPOSITION FOR ORAL CAVITY

CROSS REFERENCE TO PRIOR APPLICATION

This application is a Bypass Continuation-In-Part of PCT International Patent Application No. PCT/JP2019/041444 (filed on Oct. 23, 2019) under 35 U.S.C. § 111, which claims priority to Japanese Patent Application Nos. 2018-199776 (filed on Oct. 24, 2018), 2018-199779 (filed on Oct. 24, 2018), 2018-199781 (filed on Oct. 24, 2018), and 2018-199784 (filed on Oct. 24, 2018), which are all hereby incorporated by reference in their entirety.

TECHNICAL FIELD

The present invention relates to an oral composition and the like, and more specifically an oral emulsion composition and the like.

BACKGROUND ART

Compositions with a relatively lower water content and a relatively larger hydrocarbon oil content generally have poor stability over time. Even if such compositions are emulsified with an emulsifier, the hydrocarbon oil is often separated after long-term storage. Therefore, it is difficult to use these compositions for various applications (e.g., oral compositions).

CITATION LIST

Patent Literature

PTL 1: JP2014-189550A
PTL 2: JP2009-95253A

SUMMARY OF INVENTION

Technical Problem

An object of the present invention is to provide an oral composition that has excellent stability over time although a hydrocarbon oil is contained therein.

Solution to Problem

The present inventors found the possibility that a composition comprising a hydrocarbon oil, a polyhydric alcohol, and a surfactant has excellent stability over time although the hydrocarbon oil is contained therein. Upon further improvement, the present invention has been completed.

The present invention includes, for example, the main subjects described in the following items.

Item 1.

An oral composition comprising a hydrocarbon oil, a polyhydric alcohol, and a surfactant, the oral composition comprising:

(i) glycerol, and a polyglycerol fatty acid ester and/or an alkyl glucoside, (ii) propanediol, and a polyoxyethylene hardened castor oil and/or a polyoxyethylene hardened castor oil fatty acid ester, (iii) butylene glycol, and a polyoxyethylene alkyl ether and/or a polyoxyethylene hardened castor oil fatty acid ester, or (iv) polyethylene glycol and a polyoxyethylene hardened castor oil fatty acid ester.

Item 2.

The oral composition according to Item 1, which has a water content of 5 mass % or less.

Item 3.

The oral composition according to Item 1 or 2, which is a non-aqueous composition.

Item 4.

The oral composition according to any one of Items 1 to 3, which is not phase-separated after being allowed to stand at 25° C. for one week after preparation.

Item 5.

The oral composition according to any one of Items 1 to 4, wherein the hydrocarbon oil is paraffin.

Item 6.

A composition that is a carrier for an oral composition and comprises a hydrocarbon oil, a polyhydric alcohol, and a surfactant, the composition comprising:

(i) glycerol, and a polyglycerol fatty acid ester and/or an alkyl glucoside, (ii) propanediol, and a polyoxyethylene hardened castor oil and/or a polyoxyethylene hardened castor oil fatty acid ester, (iii) butylene glycol, and a polyoxyethylene alkyl ether and/or a polyoxyethylene hardened castor oil fatty acid ester, or (iv) polyethylene glycol and a polyoxyethylene hardened castor oil fatty acid ester.

Item 7.

The oral composition according to any one of Items 1 to 5, which is a toothbrush composition.

Item 8.

The oral composition according to any one of Items 1 to 5 and 7, comprising:

(A) a hydrocarbon oil, (B) a polyhydric alcohol, and (C) a polyglycerol fatty acid ester and/or an alkyl glucoside;

wherein (I) component (C) has an HLB of 12 or more and 18 or less, and the content mass ratio (B/A) of components (A) and (B) is 0.1 to 0.8, or (II) component (C) has an HLB of 11 or more and less than 12, and B/A is 0.4 to 3.7.

Item 9.

The oral composition according to any one of Items 1 to 5, which is an interdental brush composition.

Item 10.

The oral composition according to any one of Items 1 to 5 and 9, comprising:

(A) a hydrocarbon oil, (B) a polyhydric alcohol, and (C) a polyglycerol fatty acid ester;

wherein (III) component (C) has an HLB of 13 or more and 18 or less, and the content mass ratio (B/A) of components (A) and (B) is 0.4 to 1.1, or (IV) component (C) has an HLB of 12 or more and less than 13, and B/A is 0.1 to 1.1.

Advantageous Effects of Invention

It is possible to provide an oral composition that has excellent stability over time although a hydrocarbon oil is contained therein. Further, it is possible to provide an oral emulsion composition that has excellent stability over time although a hydrocarbon oil is contained therein. Moreover, it is possible to provide, for example, a toothbrush composition that has excellent stability over time although a hydrocarbon oil is contained therein. In addition, it is possible to provide, for example, an interdental brush composition that has excellent stability over time although a hydrocarbon oil is contained therein.

DESCRIPTION OF EMBODIMENTS

Embodiments included in the present invention are described in more detail below. The present invention preferably includes an oral composition, a method for producing the composition, and the like, but is not limited thereto. The present invention includes all of the contents disclosed in the present specification.

The oral composition included in the present invention comprises (A) a hydrocarbon oil, (B) a polyhydric alcohol, and (C) a surfactant. The oral composition of the present invention comprises (i) glycerol, and a polyglycerol fatty acid ester and/or an alkyl glucoside, (ii) propanediol, and a polyoxyethylene hardened castor oil and/or a polyoxyethylene hardened castor oil fatty acid ester, (iii) butylene glycol, and a polyoxyethylene alkyl ether and/or a polyoxyethylene hardened castor oil fatty acid ester, or (iv) polyethylene glycol and a polyoxyethylene hardened castor oil fatty acid ester. Hereinafter, this oral composition is also referred to as "the oral composition of the present invention." The above components (A) to (C) are also referred to, for example, as "component (A)," "component (B)," and "component (C)," respectively.

The use of combinations of the polyhydric alcohols and surfactants of (i) to (iv) can provide oral compositions that have excellent stability over time although a hydrocarbon oil is contained therein. In (i), the polyhydric alcohol (B) is glycerol, and the surfactant (C) is a polyglycerol fatty acid ester and an alkyl glucoside. In (ii), the polyhydric alcohol (B) is propanediol, and the surfactant (C) is a polyoxyethylene hardened castor oil and a polyoxyethylene hardened castor oil fatty acid ester. In (iii), the polyhydric alcohol (B) is butylene glycol, and the surfactant (C) is a polyoxyethylene alkyl ether and a polyoxyethylene hardened castor oil fatty acid ester. In (iv), the polyhydric alcohol (B) is polyethylene glycol, and the surfactant (C) is a polyoxyethylene hardened castor oil fatty acid ester. As long as the effects of the present invention are not impaired, polyhydric alcohols and surfactants other than the polyhydric alcohols and surfactants described in (i) to (iv) may be contained as components (B) and (C).

The oral composition of the present invention can be preferably used for toothbrushes.

In the present invention, the toothbrush preferably comprises a head portion planted with a plurality of bristle bundles, a handle portion as a handle, and a neck portion that connects the head portion and the handle portion.

Further, the oral composition of the present invention can be preferably used for interdental brushes.

Interdental brushes are known as tools for cleaning away debris between teeth or between teeth and gums. In the present invention, the interdental brush preferably comprises a handle portion including a grip portion for the user to grip, a core material joined to the handle portion, and a filament bundle implanted on the core material. The brush length of the interdental brush is, for example, preferably about 8 to 14 mm, and more preferably about 10 to 12 mm. The brush tip diameter of the interdental brush is, for example, preferably about 1.5 to 3.2 mm, and more preferably about 2.0 to 2.5 mm. The brush rear end diameter of the interdental brush is, for example, preferably about 1.5 to 7.0 mm, and more preferably about 2.0 to 4.0 mm. The minimum passing diameter of the interdental brush is, for example, preferably about 2.0 mm$\phi$ or less, and more preferably about 1.4 mm$\phi$. The brush tip diameter of the interdental brush is the diameter of the brush tip of the interdental brush, and the brush rear end diameter of the interdental brush is the diameter of the brush end of the interdental brush on the handle portion side.

As oral compositions used together with toothbrushes or interdental brushes, toothbrushes have a brush implanted on one side of the handle; thus, oral compositions that keep their shape on the wiping surface of the brush are suitable. In contrast, in interdental brushes, the area of the brush part on which the oral composition is to be placed is very small, and a short brush is attached radially around a wire; thus, oral compositions that spread over all the bristles and remain without dripping are suitable.

The propanediol can be either propylene glycol (1,2-propanediol) or 1,3-propanediol. The butylene glycol is preferably 1,3-butylene glycol.

The number average molecular weight of the polyethylene glycol is not particularly limited, but is, for example, preferably about 100 to 10000, and more preferably about 200 to 5000. Further, the polyethylene glycol used in the present invention is preferably liquid. The number average molecular weight of the polyethylene glycol is calculated based on the hydroxyl value measured according to JIS K 1557.

When the oral composition of the present invention is an oral composition comprising a hydrocarbon oil, a polyhydric alcohol, and a surfactant, and comprising (i) glycerol, and a polyglycerol fatty acid ester and/or an alkyl glucoside, it is preferable that this oral composition does not contain polyethylene glycol having a number average molecular weight of 1000 to 30000, 1500 to 25000, or more than 2000 and 20000 or less.

The polyglycerol fatty acid ester is preferably, for example, an ester compound of a $C_{8-24}$ (8, 9, 10, 11, 12, 13, 14, 15, 16, 17, 18, 19, 20, 21, 22, 23, or 24) saturated or unsaturated fatty acid and polyglycerol.

The number of carbon atoms in this fatty acid is more preferably 8 to 22, even more preferably 10 to 20, and still even more preferably 10 to 18. The fatty acid may be a saturated fatty acid or an unsaturated fatty acid. In the case of an unsaturated fatty acid, the number of carbon-carbon double bonds is preferably 1, 2, 3, or 4, and more preferably 1 or 2. Further, the fatty acid may be a linear fatty acid or a branched fatty acid. Preferred examples of such fatty acids include capric acid, lauric acid, myristic acid, stearic acid, palmitic acid, palmitoleic acid, margaric acid, oleic acid, linoleic acid, behenic acid, isocapric acid, isolauric acid, isomyristic acid, isostearic acid, isopalmitic acid, isopalmitoleic acid, isomargaric acid, isooleic acid, isolinolic acid, isobehenic acid, and the like; more preferred of these are capric acid, lauric acid, myristic acid, stearic acid, palmitic acid, oleic acid, and isostearic acid. In addition, natural fatty acids, such as coconut oil fatty acid and palm oil fatty acid, including these fatty acids, may also be used.

The polyglycerol fatty acid ester is preferably a mono-, di-, tri-, tetra-, penta-, or cycloester compound of a fatty acid mentioned above and polyglycerol, and more preferably a mono-, di-, or triester compound. In particular, when the oral composition of the present invention is a toothbrush composition or an interdental brush composition, the polyglycerol fatty acid ester is more preferably a mono- or diester compound.

The polyglycerol preferably contains 4 to 12 (4, 5, 6, 7, 8, 9, 10, 11, or 12) glycerol units ($-OCH_2CH(OH)CH_2-$) on average, and more preferably 5 to 10 glycerol units on average.

Specific preferred examples of polyglycerol fatty acid esters include polyglyceryl-$n^1$ caprate, polyglyceryl-$n^1$ laurate, polyglyceryl-$n^1$ myristate, polyglyceryl-$n^1$ stearate, polyglyceryl-$n^1$ oleate, polyglyceryl-$n^1$ dimyristate, polyglyceryl-$n^1$ distearate, polyglyceryl-$n^1$ diisostearate, polyglyceryl-$n^1$ trilaurate, polyglyceryl-$n^1$ trimyristate ($n^1$ represents the number of glycerol units, which is preferably 4 to 12, and particularly preferably 5 or 10, as described above), and the like. When the oral composition of the present invention is a toothbrush composition, specific more preferred examples of polyglycerol fatty acid esters include polyglyceryl-$n^1$ caprate, polyglyceryl-$n^1$ laurate, polyglyceryl-$n^1$ myristate, polyglyceryl-$n^1$ stearate, polyglyceryl-$n^1$ oleate, polyglyceryl-$n^1$ dimyristate, polyglyceryl-$n^1$ distearate, polyglyceryl-$n^1$ diisostearate ($n^1$ represents the number of glycerol units, which is preferably 4 to 12, and particularly preferably 5 or 10, as described above), and the like. When the oral composition of the present invention is an interdental brush composition, specific more preferred examples of polyglycerol fatty acid esters include polyglyceryl-$n^1$ caprate, polyglyceryl-$n^1$ laurate, polyglyceryl-$n^1$ myristate, polyglyceryl-$n^1$ stearate, polyglyceryl-$n^1$ oleate, polyglyceryl-$n^1$ dimyristate, polyglyceryl-$n^1$ diisostearate ($n^1$ represents the number of glycerol units, which is preferably 4 to 12, and particularly preferably 5 or 10, as described above), and the like. The polyglycerol fatty acid esters can be used singly or in combination of two or more.

The alkyl glycoside is a compound having a structure in which a higher alcohol and sugar are linked through a glycoside bond.

The higher alcohol is, for example, preferably a $C_{6-18}$ (6, 7, 8, 9, 10, 11, 12, 13, 14, 15, 16, 17, or 18) alkyl alcohol, and more preferably a $C_{8-16}$ alkyl alcohol. The alkyl alcohol may be linear or branched, and is preferably linear. Further, the number of OH groups in the alkyl alcohol is preferably 1.

The sugar, which is linked to a higher alcohol through a glycoside bond, may be a monosaccharide or a polysaccharide. In the case of a polysaccharide, preferred examples include di- to hexasaccharides (di-, tri-, tetra-, penta-, and hexasaccharides); more preferred of these are di- or trisaccharides. Examples of monosaccharides include glucose, maltose, and the like; preferred of these is glucose. Further, the polysaccharide is preferably, for example, one in which at least one member selected from the group consisting of glucose and maltose is multiply linked through a glycoside bond, and particularly preferably one in which glucose is linked through a glycoside bond. The glycoside bond can be an α- or β-glycoside bond. The alkyl glucosides can be used singly or in combination of two or more.

The polyoxyethylene hardened castor oil is preferably a POE($n^3$) hardened castor oil ($n^3$ represents the average number of moles of EO added, which is preferably about 10 to 150, more preferably about 15 to 130, and even more preferably about 20 to 120). This can also be referred to as "PEG-$n^3$ hydrogenated castor oil." The polyoxyethylene hardened castor oils can be used singly or in combination of two or more.

The polyoxyethylene hardened castor oil fatty acid ester is preferably an ester compound of a POE($n^4$) hardened castor oil ($n^4$ represents the average number of moles of EO added, which is preferably about 3 to 70, more preferably about 4 to 60, and even more preferably about 5 to 50; this can also be referred to as "PEG-$n^4$ hydrogenated castor oil") and, for example, a $C_{8-24}$ (8, 9, 10, 11, 12, 13, 14, 15, 16, 17, 18, 19, 20, 21, 22, 23, or 24) saturated or unsaturated fatty acid. The number of carbon atoms in this fatty acid is more preferably 8 to 22, even more preferably 10 to 20, and still even more preferably 12 to 18. The fatty acid may be a saturated fatty acid or an unsaturated fatty acid. In the case of an unsaturated fatty acid, the number of carbon-carbon double bonds is preferably 1, 2, 3, or 4, and more preferably 1 or 2. Further, the fatty acid may be a linear fatty acid or a branched fatty acid. Preferred examples of such fatty acids include capric acid, lauric acid, myristic acid, stearic acid, palmitic acid, palmitoleic acid, margaric acid, oleic acid, linoleic acid, behenic acid, isocapric acid, isolauric acid, isomyristic acid, isostearic acid, isopalmitic acid, isopalmitoleic acid, isomargaric acid, isooleic acid, isolinolic acid, isobehenic acid, and the like; more preferred of these are capric acid, lauric acid, myristic acid, stearic acid, oleic acid, and isostearic acid. In addition, natural fatty acids, such as coconut oil fatty acid and palm oil fatty acid, including these fatty acids, may also be used.

The polyoxyethylene hardened castor oil fatty acid ester is preferably a mono-, di-, tri-, tetra-, penta-, or cycloester compound of a fatty acid mentioned above and a POE($n^4$) hardened castor oil, and more preferably a mono-, di-, or triester compound.

Specific preferred examples of polyoxyethylene hardened castor oil fatty acid esters include polyoxyethylene($n^4$) hardened castor oil laurate, polyoxyethylene($n^4$) hardened castor oil isostearate, polyoxyethylene($n^4$) hardened castor oil tri-isostearate ($n^4$ represents the average number of moles of EO added, which is preferably about 3 to 70, more preferably about 4 to 60, and even more preferably about 5 to 50, as described above), and the like. The polyoxyethylene hardened castor oil fatty acid esters can be used singly or in combination of two or more.

In the polyoxyethylene alkyl ether, the number of carbon atoms in the alkyl group is preferably 8 to 24 (8, 9, 10, 11, 12, 13, 14, 15, 16, 17, 18, 19, 20, 21, 22, 23, or 24), more preferably 8 to 22, even more preferably 10 to 20, and still even more preferably 12 to 18. The alkyl group may be linear or branched, and is preferably linear.

The average number of moles of the ethylene oxide unit (EO) added is preferably about 2 to 100, more preferably about 2 to 50, and even more preferably about 2 to 40.

Specific preferred examples of polyoxyethylene alkyl ethers include POE($n^5$) lauryl ether, POE($n^5$) cetyl ether, POE($n^5$) stearyl ether, POE($n^5$) behenyl ether, POE($n^5$) oleyl ether ($n^5$ represents the average number of moles of EO added, which is preferably about 2 to 100, more preferably about 2 to 50, and even more preferably about 2 to 40, as described above), and the like. The polyoxyethylene alkyl ethers can be used singly or in combination of two or more.

Usable surfactants other than the surfactants described in (i) to (iv) are not particularly limited as long as the effects of the present invention are not impaired. Nonionic surfactants are preferable, and more specific examples include polyethylene glycol fatty acid esters, polyoxyethylene sorbitan fatty acid esters, polyoxyethylene fatty acid glyceryl, polyoxyethylene polyoxypropylene alkyl ethers, polyoxyethylene sterol, and the like.

The hydrophilic-lipophilic balance (HLB) of the surfactants, including the surfactants described in (i) to (iv), is not particularly limited as long as the effects of the present invention are not impaired. For example, the HLB is preferably about 7 to 18. The upper or lower limit of this range may be, for example, 7.5, 8, 8.5, 9, 9.5, 10, 10.5, 11, 11.5, 12, 12.5, 13, 13.5, 14, 14.5, 15, 15.5, 16, 16.5, 17, or 17.5. When the oral composition of the present invention is a toothbrush composition, the HLB of component (C) used is preferably, for example, about 11 to 18. The upper or lower limit of this range may be, for example, 11.5, 12, 12.5, 13, 13.5, 14, 14.5, 15, 15.5, 16, 16.5, 17, or 17.5. When the oral composition of the present invention is an interdental brush composition, the HLB of component (C) used is preferably, for example, about 12 to 18. The upper or lower limit of this range may be, for example, 12.5, 13, 13.5, 14, 14.5, 15, 15.5, 16, 16.5, 17, or 17.5.

The polyethylene glycol fatty acid ester is preferably, for example, an ester compound of a $C_{8-24}$ (8, 9, 10, 11, 12, 13, 14, 15, 16, 17, 18, 19, 20, 21, 22, 23, or 24) saturated or unsaturated fatty acid and a polyethylene glycol ether.

The number of carbon atoms in this fatty acid is more preferably 8 to 22, even more preferably 10 to 20, and still even more preferably 12 to 18. The fatty acid may be a saturated fatty acid or an unsaturated fatty acid. In the case of an unsaturated fatty acid, the number of carbon-carbon double bonds is preferably 1, 2, 3, or 4, and more preferably 1 or 2. Further, the fatty acid may be a linear fatty acid or a branched fatty acid. Preferred examples of such fatty acids include capric acid, lauric acid, myristic acid, stearic acid, palmitic acid, palmitoleic acid, margaric acid, oleic acid, linoleic acid, behenic acid, isocapric acid, isolauric acid, isomyristic acid, isostearic acid, isopalmitic acid, isopalmitoleic acid, isomargaric acid, isooleic acid, isolinolic acid, isobehenic acid, and the like; more preferred of these are capric acid, lauric acid, myristic acid, stearic acid, oleic acid, and isostearic acid. In addition, natural fatty acids, such as coconut oil fatty acid and palm oil fatty acid, including these fatty acids, may also be used.

In the polyethylene glycol, the average number of moles of the ethylene oxide unit (EO) added is preferably about 2 to 150, more preferably about 10 to 140, and even more preferably about 20 to 130.

The polyethylene glycol fatty acid ester is preferably a mono-, di-, tri-, tetra-, penta-, or cycloester compound of a fatty acid mentioned above and polyethylene glycol, and more preferably a mono- or diester compound.

Specific preferred examples of polyethylene glycol fatty acid esters include polyethylene glycol-$n^6$ monolaurate, polyethylene glycol-$n^6$ monostearate, polyethylene glycol-$n^6$ monooleate, polyethylene glycol-$n^6$ monoisostearate, polyethylene glycol-$n^6$ dilaurate, polyethylene glycol-$n^6$ distearate, polyethylene glycol-$n^6$ dioleate, polyethylene glycol-$n^6$ diisostearate ($n^6$ represents the average number of moles of EO added, which is preferably about 2 to 150, more preferably about 10 to 140, and even more preferably about 20 to 130, as described above), and the like.

The polyoxyethylene sorbitan fatty acid ester is preferably, for example, an ester compound of a $C_{8-24}$ (8, 9, 10, 11, 12, 13, 14, 15, 16, 17, 18, 19, 20, 21, 22, 23, or 24) saturated or unsaturated fatty acid and a polyethylene glycol ether of sorbitol.

The number of carbon atoms in this fatty acid is more preferably 8 to 22, even more preferably 10 to 20, and still even more preferably 12 to 18. The fatty acid may be a saturated fatty acid or an unsaturated fatty acid. In the case of an unsaturated fatty acid, the number of carbon-carbon double bonds is preferably 1, 2, 3, or 4, and more preferably 1 or 2. Further, the fatty acid may be a linear fatty acid or a branched fatty acid. Preferred examples of such fatty acids include capric acid, lauric acid, myristic acid, stearic acid, palmitic acid, palmitoleic acid, margaric acid, oleic acid, linoleic acid, behenic acid, isocapric acid, isolauric acid, isomyristic acid, isostearic acid, isopalmitic acid, isopalmitoleic acid, isomargaric acid, isooleic acid, isolinolic acid, isobehenic acid, and the like; more preferred of these are capric acid, lauric acid, myristic acid, stearic acid, oleic acid, and isostearic acid. In addition, natural fatty acids, such as coconut oil fatty acid and palm oil fatty acid, including these fatty acids, may also be used.

In the polyoxyethylene, the average number of moles of the ethylene oxide unit (EO) added is preferably about 20 to 80, more preferably about 25 to 70, and even more preferably about 30 to 60.

The polyoxyethylene sorbitan fatty acid ester is preferably a mono-, di-, tri-, tetra-, penta-, or cycloester compound of a fatty acid mentioned above and a polyethylene glycol ether of sorbitol, and more preferably a tri- or tetraester compound.

Specific preferred examples of polyoxyethylene sorbitan fatty acid esters include solves-$n^7$ tetraoleate ($n^7$ represents the average number of moles of EO added, which is preferably about 20 to 80, more preferably about 25 to 70, and even more preferably about 30 to 60, as described above) and the like.

The polyoxyethylene fatty acid glyceryl is a polyethylene glycol ether of fatty acid glyceryl (monoester of a fatty acid and glycerol), and is preferably, for example, one in which polyethylene glycol is bonded (ether-bonded) to a monoester of a $C_{8-24}$ (8, 9, 10, 11, 12, 13, 14, 15, 16, 17, 18, 19, 20, 21, 22, 23, or 24) saturated or unsaturated fatty acid and glycerol.

The number of carbon atoms in this fatty acid is more preferably 8 to 22, even more preferably 10 to 20, and still even more preferably 12 to 18. The fatty acid may be a saturated fatty acid or an unsaturated fatty acid. In the case of an unsaturated fatty acid, the number of carbon-carbon double bonds is preferably 1, 2, 3, or 4, and more preferably 1 or 2. Further, the fatty acid may be a linear fatty acid or a branched fatty acid. Preferred examples of such fatty acids include capric acid, lauric acid, myristic acid, stearic acid, palmitic acid, palmitoleic acid, margaric acid, oleic acid, linoleic acid, behenic acid, isocapric acid, isolauric acid, isomyristic acid, isostearic acid, isopalmitic acid, isopalmitoleic acid, isomargaric acid, isooleic acid, isolinolic acid, isobehenic acid, and the like; more preferred of these are capric acid, lauric acid, myristic acid, stearic acid, oleic acid, and isostearic acid. In addition, natural fatty acids, such as coconut oil fatty acid and palm oil fatty acid, including these fatty acids, may also be used.

In the polyoxyethylene, the average number of moles of the ethylene oxide unit (EO) added is preferably about 3 to 200, more preferably about 5 to 50, and even more preferably about 5 to 30.

The polyoxyethylene fatty acid glyceryl is preferably one in which only one of the two hydroxyl groups of fatty acid glyceryl is ether-bonded to polyethylene glycol.

Specific preferred examples of polyoxyethylene fatty acid glyceryl include PEG-$n^8$ glyceryl stearate ($n^8$ represents the average number of moles of EO added, which is preferably about 3 to 200, more preferably about 5 to 50, and even more preferably about 5 to 30, as described above) and the like.

In the polyoxyethylene polyoxypropylene alkyl ether, the number of carbon atoms in the alkyl group is preferably 8 to 24 (8, 9, 10, 11, 12, 13, 14, 15, 16, 17, 18, 19, 20, 21, 22, 23, or 24), more preferably 8 to 22, even more preferably 10 to 20, and still even more preferably 12 to 18. Further, the alkyl group may be liner or branched.

The average number of moles of the ethylene oxide unit (EO) added is preferably about 2 to 100, more preferably about 2 to 50, and even more preferably about 2 to 40. Further, the average number of moles of propylene oxide unit (PO) added is preferably about 2 to 12, more preferably about 2 to 10, and even more preferably about 4 to 8.

Specific preferred examples of polyoxyethylene polyoxypropylene alkyl ethers include PPG-y ceteth-x, PPG-y decyltetradeceth-x (x represents the average number of moles of EO added, which is preferably about 2 to 100, more preferably about 2 to 50, and even more preferably about 2 to 40, as described above; and y represents the average number of moles of PO added, which is preferably about 2 to 12, more preferably about 2 to 10, and even more preferably about 4 to 8, as described above), and the like.

The polyoxyethylene sterol is preferably PEG-$n^9$ phytosterol ($n^9$ represents the average number of moles of EO added, which is preferably about 5 to 100, more preferably about 5 to 50, and even more preferably about 10 to 40).

When the oral composition of the present invention is a toothbrush composition, it is more preferable to use a polyglycerol fatty acid ester and/or an alkyl glucoside as the surfactant (C).

When the oral composition of the present invention is an interdental brush composition, it is more preferable to use a polyglycerol fatty acid ester as the surfactant (C).

Examples of the hydrocarbon oil (A) include paraffin, squalane, microcrystalline wax, petrolatum, ceresin, limonene, turpentine oil, and the like; in particular, known hydrocarbon oils used for oral compositions are preferable. Of these, squalane and paraffin are preferable, and paraffin is particularly preferable. As the squalane, animal squalane and vegetable squalane can both be used. For example, shark squalane, olive squalane, and the like can be preferably used. Further, the paraffin is preferably liquid paraffin, and particularly more preferably light liquid paraffin. The hydrocarbon oils can be used singly or in combination of two or more.

Regarding the content ratio of the hydrocarbon oil (A) and the polyhydric alcohol (B) in the oral composition of the present invention, for example, the amount of the hydrocarbon oil (A) is preferably about 0.10 to 10 parts by mass, more preferably about 0.13 to 8 parts by mass, and even more preferably about 0.15 to 5 parts by mass, per part by mass of the polyhydric alcohol (B). In other words, the content mass ratio (B/A) of components (A) and (B) in the oral composition of the present invention is preferably about 0.1 to 18, preferably about 0.10 to 10, more preferably about 0.13 to 7.6, and even more preferably about 0.2 to 6.6. Further, regarding the content mass ratio (B/A) of components (A) and (B) in the oral composition of the present invention, (V) when component (C) has an HLB of 12 or more and 18 or less, B/A is preferably 0.1 or more and 18 or less. The upper or lower limit of this range may be, for example, 0.2, 0.3, 0.4, 0.5, 0.6, 0.7, 0.8, 0.9, 1.0, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, or 17.5. Moreover, (VI) when component (C) has an HLB of 11 or more and less than 12, B/A is preferably 0.4 or more and 18 or less. The upper or lower limit of this range may be, for example, 0.5, 0.6, 0.7, 0.8, 0.9, 1.0, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, or 17.5. Furthermore, (VII) when component (C) has an HLB of 10 or more and less than 11, B/A is preferably 1.3 or more and 18 or less. The upper or lower limit of this range may be, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, or 17.5.

When the oral composition of the present invention is a toothbrush composition, regarding the content mass ratio (B/A) of components (A) and (B) in the composition, (I) when component (C) has an HLB of 12 or more and 18 or less, B/A is preferably 0.1 or more and 0.8 or less. The upper or lower limit of this range may be, for example, 0.2, 0.3, 0.4, 0.5, 0.6, or 0.7. Further, (II) when component (C) has an HLB of 11 or more and less than 12, B/A is preferably 0.4 or more and 3.7 or less. The upper or lower limit of this range may be, for example, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, or 3.6.

When the oral composition of the present invention is an interdental brush composition, regarding the content mass ratio (B/A) of components (A) and (B) in the composition, (III) when component (C) has an HLB of 13 or more and 18 or less, B/A is preferably 0.4 or more and 1.1 or less. The upper or lower limit of this range may be, for example, 0.5, 0.6, 0.7, 0.8, 0.9, or 1.0. Further, (IV) when component (C) has an HLB of 12 or more and less than 13, B/A is preferably 0.1 or more and 1.1 or less. The upper or lower limit of this range may be, for example, 0.2, 0.3, 0.4, 0.5, 0.6, 0.7, 0.8, 0.9, or 1.0.

The content mass ratio (A/C) of components (A) and (C) in the oral composition of the present invention is not particularly limited as long as the effects of the present invention are not impaired. For example, the content mass ratio (A/C) is preferably about 1 to 375. The upper or lower limit of this range may be 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 150, 200, 250, 300, or 350. Further, regarding the content ratio of components (A) and (C) in the oral composition of the present invention, for example, the amount of component (A) is about 2 to 125 parts by mass, about 3 to 110 parts by mass, or about 5 to 100 parts by mass, per part by mass of component (C). When the oral composition of the present invention is a toothbrush composition, the content mass ratio (A/C) of components (A) and (C) in the composition is not particularly limited. For example, the content mass ratio (A/C) is about 6 to 130 or about 11 to 125. When the oral composition of the present invention is an interdental brush composition, the content mass ratio (A/C) of components (A) and (C) in the composition is not particularly limited. For example, the content mass ratio (A/C) is about 9 to 130 or about 12 to 125.

Further, regarding the content ratio of polyhydric alcohol (B) and surfactant (C) in the oral composition of the present invention, for example, the amount of polyhydric alcohol is preferably about 3 to 75 parts by mass, more preferably about 7 to 60 parts by mass, and even more preferably about 8 to 50 parts by mass, per part by mass of the surfactant.

The content ratio of hydrocarbon oil and surfactant, the content ratio of polyhydric alcohol and surfactant, and the content ratio of hydrocarbon oil and polyhydric alcohol in the oral composition of the present invention are not particularly limited as long as the oral composition is prepared; however, it is preferable to satisfy one of the above content ratios, more preferably two of them, and even more preferably three of them. In particular, the content mass ratio (B/A) of components (A) and (B) is preferably as described above.

The content of component (A) in the oral composition of the present invention is not particularly limited as long as the oral composition of the present invention is prepared. The content of component (A) is preferably, for example, 3 mass % or more and less than 90 mass % based on the total mass of components (A), (B), and (C) in the oral composition of the present invention. The upper or lower limit of this range may be, for example, 5, 10, 15, 20, 25, 30, 35, 40, 45, 50, 55, 60, 65, 70, 75, 80, or 85. For example, the content of component (A) is about 3 to 85 mass %, about 5 to 80 mass %, or about 15 to 75 mass %, based on the total mass of components (A), (B), and (C). When the oral composition of the present invention is a toothbrush composition, the content of component (A) in the composition is not particularly limited as long as the effects of the present invention are not impaired. The content of component (A) is preferably, for example, 25 mass % or more and less than 90 mass % based on the total mass of components (A), (B), and (C). The upper or lower limit of this range may be, for example, 30, 35, 40, 45, 50, 55, 60, 65, 70, 75, 80, or 85. When the oral composition of the present invention is an interdental brush composition, the content of component (A) in the composition is not particularly limited as long as the effects of the present invention are not impaired. The content of component (A) is preferably, for example, 45 mass % or more and less than 90 mass % based on the total mass of components (A), (B), and (C). The upper or lower limit of this range may be, for example, 50, 55, 60, 65, 70, 75, 80, or 85.

The content of component (B) in the oral composition of the present invention is not particularly limited as long as the oral composition of the present invention is prepared. The content of component (B) is preferably, for example, 7 mass % or more and 95 mass % or less based on the total mass of components (A), (B), and (C) in the oral composition of the present invention. The upper or lower limit of this range may be, for example, 10, 15, 20, 25, 30, 35, 40, 45, 50, 55, 60, 65, 70, 75, 80, 85, or 90. For example, the content of component (B) is about 7 to 95 mass %, about 15 to 90 mass %, or about 20 to 80 mass %, based on the total mass of components (A), (B), and (C). When the oral composition of the present invention is a toothbrush composition, the content of component (B) in the composition is not particularly limited as long as the effects of the present invention are not impaired. The content of component (B) is preferably, for example, 7 mass % or more and 70 mass % or less based on the total mass of components (A), (B), and (C). The upper or lower limit of this range may be, for example, 10, 15, 20, 25, 30, 35, 40, 45, 50, 55, 60, or 65. When the oral composition of the present invention is an interdental brush composition, the content of component (B) in the composition is not particularly limited as long as the effects of the present invention are not impaired. The content of component (B) is preferably, for example, 7 mass % or more and 70 mass % or less based on the total mass of components (A), (B), and (C). The upper or lower limit of this range may be, for example, 10, 15, 20, 25, 30, 35, 40, 45, 50, 55, 60, or 65.

The content of component (C) in the oral composition of the present invention is not particularly limited as long as the oral composition of the present invention is prepared. The amount of component (C) is preferably, for example, 0.3 mass % or more and 7 mass % or less based on the total mass of components (A), (B), and (C) in the oral composition of the present invention. The upper or lower limit of this range may be, for example, 0.5, 1, 1.5, 2, 2.5, 3, 3.5, 4, 4.5, 5.5, 6, or 6.5. For example, the content of component (C) is about 0.3 to 7 mass %, about 0.5 to 6 mass %, or about 1 to 5 mass %, based on the total mass of components (A), (B), and (C). When the oral composition of the present invention is a toothbrush composition, the content of component (C) in the composition is not particularly limited as long as the effects of the present invention are not impaired. The content of component (C) is preferably, for example, 0.3 mass % or more and 7 mass %, or less based on the total mass of components (A), (B), and (C). The upper or lower limit of this range may be, for example, 0.5, 1, 1.5, 2, 2.5, 3, 3.5, 4, 4.5, 5.5, 6, or 6.5. When the oral composition of the present invention is an interdental brush composition, the content of component (C) in the composition is not particularly limited as long as the effects of the present invention are not impaired. The content of component (C) is preferably, for example, 0.3 mass % or more and 7 mass % or less based on the total mass of components (A), (B), and (C). The upper or lower limit of this range may be, for example, 0.5, 1, 1.5, 2, 2.5, 3, 3.5, 4, 4.5, 5.5, 6, or 6.5.

These content ratios (content mass ratios) and contents are values calculated based on the contents of the polyhydric alcohols and surfactants described in (i) to (iv). Specifically, in (i), these values are calculated based on the contents of glycerol as component (B) and a polyglycerol fatty acid ester and an alkyl glucoside as component (C). In (ii), these values are calculated based on the contents of propanediol as component (B) and a polyoxyethylene hardened castor oil and a polyoxyethylene hardened castor oil fatty acid ester as component (C). In (iii), these are calculated based on the contents of butylene glycol as component (B) and a polyoxyethylene alkyl ether and a polyoxyethylene hardened castor oil fatty acid ester as component (C). In (iv), these values are calculated based on the contents of polyethylene glycol as component (B) and a polyoxyethylene hardened castor oil fatty acid ester as component (C).

When the oral composition of the present invention is a toothbrush composition, it is preferable that the oral composition comprises (A) a hydrocarbon oil, (B) a polyhydric alcohol, and (C) a polyglycerol fatty acid ester and/or an alkyl glucoside. Further, it is preferable that (I) component (C) has an HLB of 12 or more and 18 or less, and the content mass ratio (B/A) of components (A) and (B) is 0.1 to 0.8, or that (II) component (C) has an HLB of 11 or more and less than 12, and B/A is 0.4 to 3.7.

When the oral composition of the present invention is an interdental brush composition, it is preferable that the oral composition comprises (A) a hydrocarbon oil, (B) a polyhydric alcohol, and (C) a polyglycerol fatty acid ester. Further, it is preferable that (III) component (C) has an HLB of 13 or more and 18 or less, and the content mass ratio (B/A) of components (A) and (B) is 0.4 to 1.1, or that (IV) component (C) has an HLB of 12 or more and less than 13, and B/A is 0.1 to 1.1.

The oral composition of the present invention may contain water within the range in which the effects of the present invention are not impaired. Specifically, for example, the water content is preferably 5 mass % or less. Further, the upper limit of the water content may be 4, 3, 2, 1, or 0.5 mass %. It is more preferable that the oral composition of the present invention is a composition that does not contain water (i.e., a non-aqueous composition). However, if the composition contains water as an unavoidable impurity in an amount that is difficult to remove, it is included in the "non-aqueous composition."

The oral composition of the present invention is preferably an emulsion composition. Further, the oral composition of the present invention is preferably such that the hydrocarbon oil is not separated (not phase-separated) particularly when the oral composition is allowed to stand at room temperature (25° C.) for one week after preparation, and more preferably when the oral composition is allowed to stand at room temperature (25° C.) for one month after preparation. The oral composition of the present invention is not particularly limited in its shape, but is preferably, for example, gel-like or cream-like.

The method for preparing the oral composition of the present invention is, for example, a method of first stirring and mixing a polyhydric alcohol and a surfactant, and then gradually adding a hydrocarbon oil to the mixture while continuing to stir. Mixing can be carried out using a known stirrer (e.g., a dispersion mixer). If a large amount of hydrocarbon oil is added at one time, it may not be uniformly mixed; thus, it is preferable to gradually add the hydrocarbon oil.

The oral composition of the present invention can be formed into general dosage forms, such as dentifrices (e.g., toothpaste), liquid dentifrices, mouthwashes, gels, ointments, dermatological pastes, gums, and the like according to a general method, but are not limited thereto.

The oral composition of the present invention may contain known components that can be contained in oral compositions within the range in which the effects of the present invention are not impaired. The oral composition of the present invention containing such components can be prepared, for example, by adding these components when stirring and mixing a polyhydric alcohol and a surfactant.

Examples of such known components include abrasives, wetting agents, foaming agents, fragrances, activators, sweeteners, preservatives, colorants, pH adjusters, stabilizers, flavoring agents, astringents, thickeners, other medicinal agents, and the like. Such known components can be used singly or in combination of two or more.

Usable examples of abrasives include dicalcium phosphate dihydrate and anhydride, calcium phosphate, tricalcium phosphate, calcium carbonate, calcium pyrophosphate, aluminum hydroxide, alumina, silicic anhydride, silica gel, aluminum silicate, calcium silicate, insoluble sodium metaphosphate, trimagnesium phosphate, magnesium carbonate, calcium sulfate, methyl polymethacrylate, bentonite, zirconium silicate, hydroxyapatite, synthetic resin, bioactive glass, and the like.

Examples of wetting agents include alcohols (monohydric alcohol or polyhydric alcohol), and more specifically, for example, ethanol. Further, preferred examples of polyhydric alcohols include divalent or trivalent alcohols. Divalent and trivalent alcohols are not particularly limited, and preferred examples include ethylene glycol, propanediol, diethylene glycol, polyethylene glycol, 1,3-butylene glycol, glycerol, and the like. As the propanediol, propylene glycol (1,2-propanediol) and 1,3-propanediol can both be preferably used. Of these, propylene glycol, 1,3-propanediol, 1,3-butylene glycol, and glycerol are preferable; and propylene glycol and glycerol are particularly preferable.

Examples of foaming agents include higher alkyl sulfate ester salts having a $C_{8-18}$ alkyl group, such as sodium lauryl sulfate and sodium myristyl sulfate; N-long-chain acylamino acid salts, α-olefin sulfonate salts, higher fatty acid sodium monoglyceride monosulfates, N-methyl-N-palmitoyl tauride salts, N-acylsarcosine sodium, N-acylglutamic acid salts, N-methyl-N-acyltaurine sodium, N-methyl-N-acylalanine sodium, sodium α-olefin sulfonate, and other anionic surfactants.

Examples of fragrances include menthol, anethole, carvone, eugenol, limonene, peppermint oil, spearmint oil, winter green, methyl salicylate, cineole, thymol, clove oil, eucalyptus oil, rosemary oil, sage oil, lemon oil, orange oil, ocimene oil, citronellol, methyl eugenol, and the like.

Examples of sweeteners include sodium saccharin, acesulfame potassium, stevioside, neohesperidin dihydrochalcone, glycyrrhizin, perillatin, thaumatin, aspartylphenylalanine methyl ester, α-methoxycinnamic aldehyde, xylitol, sucralose, palatinose, Steviafin, and the like.

Examples of preservatives include parabens, such as methylparaben, ethylparaben, propylparaben, and butylparaben; sodium benzoate, phenoxyethanol, alkyldiaminoethylglycine hydrochloride, and the like.

Examples of colorants include legal pigments, such as Blue No. 1, Yellow No. 4, Red No. 202, and Green No. 3; mineral pigments, such as ultramarine, reinforced ultramarine, and navy blue; titanium oxide; and the like.

Examples of pH adjusters include citric acid, phosphoric acid, malic acid, pyrophosphoric acid, lactic acid, tartaric acid, phytic acid, glycerophosphoric acid, acetic acid, nitric acid, or chemically acceptable salts thereof, sodium hydroxide, and the like.

Examples of stabilizers include sodium edetate, sodium thiosulfate, sodium sulfite, sodium chloride, calcium lactate, lanolin, triacetin, castor oil, magnesium sulfate, and the like.

Examples of flavoring agents include tea extract, tea dry distillate, propolis extract, sodium glutamate, and the like.

Examples of astringents include baking soda, aluminum lactate, zinc compounds, and the like.

Examples of thickeners include cellulose derivatives, such as hydroxyethyl cellulose, carboxymethyl cellulose, hydroxypropyl cellulose, hydroxypropyl methyl cellulose, and hydroxymethyl ethyl cellulose; gums, such as xanthan gum, locust bean gum, carrageenan, tragacanth gum, karaya gum, gum arabic, and gellan gum; synthetic binders, such as polyvinyl alcohol, sodium polyacrylate, carboxyvinyl polymer, and polyvinylpyrrolidone; inorganic binders, such as thickened silica, aluminum silica gel, and veegum; sodium alginate, pectin, agar, gelatin, soy polysaccharides, sodium chondroitin sulfate, sodium hyaluronate, and the like.

Examples of other medicinal agents include fluorine compounds such as sodium fluoride, sodium monofluorophosphate, and tin(II) fluoride; potassium salts such as potassium nitrate and potassium chloride, strontium salts such as strontium chloride, enzymes such as dextranase, mutanase, amylase, protease, and lytic enzyme; tranexamic acid, ε-aminocaproic acid, aluminum chlorohydroxy allantoin, allantoin, dihydrocholesterol, glycyrrhizic acid, glycyrrhetinic acid, bisabolol, isopropylmethylphenol, glycerophosphoric acid, chlorophyll, copper gluconate, sodium chloride, water-soluble inorganic phosphate compounds, pyrrolidone carboxylic acid, chlorhexidine salts, triclosan, cetylpyridinium chloride, benzalkonium chloride, and benzethonium chloride; vitamins such as dl-α-tocopherol acetate, pyridoxine acetate, ascorbic acid, or salts thereof; basic amino acids such as arginine, lysine, citrulline, ornithine, creatine, histidine, diaminobutanoic acid, diaminopropionic acid, or salts thereof; polyphenols such as flavonoids and phenolic acids; plant extracts such as aloe, ginkgo leaves, agaricus, oolong tea, chamomile, Chinese quince, gymnema, *Sasa veitchii*, sweet tea, Tochu tea, *Houttuynia cordata*, adlay, nikko maple, wormwood, green tea, rooibos, lemon balm, rosemary, crabmin, *Siraitia grosvenorii*, perilla, cranberry, yarrow, elder, licorice, mint, eucalyptus, guarana, glycyrrhiza, *Tilia miqueliana*, hop, cacao, mulberry leaves, thyme, and scutellaria; lactic acid bacteria, hydrogen peroxide, and the like.

The amounts of these known components can be suitably adjusted with reference to their amounts generally used in oral compositions, to the extent that they do not interfere with the effects of the present invention.

The present invention also includes a carrier for an oral composition, comprising a hydrocarbon oil, a polyhydric alcohol, and a polyglycerol fatty acid ester and/or an alkyl glucoside. The structure of the carrier for an oral composition is basically the same as that of the oral composition described above, except for its use as a carrier for an oral composition.

Components acceptable for oral compositions (e.g., known components mentioned above) can be further added to the carrier for an oral composition, thereby producing a suitable oral composition.

The term "comprising" includes "consisting essentially of" and "consisting of." Further, the present invention ated as X (evaluation of possibility of preparation). Further, the obtained compositions were each placed in a glass container, allowed to stand at room temperature (25° C.) for one week, then visually observed again, and evaluated in the same manner (one-week stability evaluation). Unless otherwise specified, those that were evaluated as ○ in the one-week stability evaluation were stable without phase separation until about one month at room temperature. The results are shown in Tables 1 and 2.

TABLE 1

| | | Change in the mixing ratio of light liquid paraffin and glycerol | | | | | | | | |
| Substance name | HLB | Example 1-1 | Example 1-2 | Example 1-3 | Example 1-4 | Example 1-5 | Example 1-6 | Example 1-7 | Example 1-8 | Example 1-9 |
|---|---|---|---|---|---|---|---|---|---|---|
| Glycerol | — | 15 | 35 | 40 | 45 | 55 | 60 | 70 | 80 | 90 |
| Light liquid paraffin | — | 80 | 60 | 55 | 50 | 40 | 35 | 25 | 15 | 5 |
| Polyglyceryl-10 laurate | 17.1 | 5 | 5 | 5 | 5 | 5 | 5 | 5 | 5 | 5 |
| Possibility of preparation | | ○ | ○ | ○ | ○ | ○ | ○ | ○ | ○ | ○ |
| 1 W stability | | ○ | ○ | ○ | ○ | ○ | ○ | ○ | ○ | ○ |
| B/A | | 0.188 | 0.583 | 0.727 | 0.900 | 1.375 | 1.714 | 2.800 | 5.333 | 18.000 | includes all of any combinations of the constituent requirements described in the present specification.

In addition, the various characteristics (properties, structures, functions, etc.) described in each embodiment of the present invention described above may be combined in any way in specifying the subject matters included in the present invention. In other words, the present invention includes all the subject matters comprising all combinations of the combinable characteristics described in the present specification.

EXAMPLES

The present invention is described in more detail below; however, the present invention is not limited to the following examples. Unless otherwise specified, "%" indicates "mass %." Further, unless otherwise specified, the amount of each component shown in the tables also indicates "mass %." Among the raw materials shown in the tables, fatty acids without wording indicating the number of bonds (e.g., di- or tri-) refer to "mono-fatty acids" (e.g., polyglyceryl-10 laurate refers to polyglyceryl-10 monolaurate). "POE" stands for polyoxyethylene, and "PEG" stands for polyethylene glycol. In the tables, "-" means "not evaluated."

Preparation 1 of Oral Composition

According to the formulations shown in Tables 1 and 2 (the numerical values indicate mass %), in addition to glycerol and light liquid paraffin, polyglyceryl-10 laurate was added to prepare oral compositions. More specifically, mixing was carried out as follows. Glycerol and polyglyceryl-10 laurate were added to a container (beaker), and these were mixed by manual stirring using a glass rod or by stirring with a dispersion mixer. In doing so, heating was performed as necessary. While continuing to stir, light liquid paraffin was gradually added. The light liquid paraffin used was Moresco White P-70 (Moresco Corporation).

Immediately after preparation, each of the obtained compositions was visually observed to confirm the presence of phase separation. Those that were not phase-separated and maintained a gel state (emulsion state) were evaluated as ○, and those in which the oil phase was separated were evalu-

TABLE 2

| | | Change in the amount of polyglyceryl-10 laurate | | | |
| Substance name | HLB | Example 1-2 | Example 2-1 | Example 2-2 | Example 2-3 |
|---|---|---|---|---|---|
| Glycerol | — | 35 | 36.25 | 37 | 37.25 |
| Light liquid paraffin | — | 60 | 61.25 | 62 | 62.25 |
| Polyglyceryl-10 laurate | 17.1 | 5 | 2.5 | 1 | 0.5 |
| Possibility of preparation | | ○ | ○ | ○ | ○ |
| 1 W stability | | ○ | ○ | ○ | ○ |
| B/A | | 0.583 | 0.592 | 0.597 | 0.598 |

It was revealed that the compositions shown in the Examples were not phase-separated, and stably maintained their emulsion state after another week.

Preparation 2 of Oral Composition

According to the formulations shown in Table 3 (the numerical values indicate mass %), in addition to glycerol and light liquid paraffin, various surfactants were added to prepare oral compositions, and their stability was evaluated in the same manner as described above. Only in Example 3-7, Moresco White P-350 (Moresco Corporation) was used as the light liquid paraffin. Moresco White P-70 is light liquid paraffin having a kinematic viscosity of 12.56 mm/s (40° C.) and an average molecular weight of 323, whereas Moresco White P-350 is light liquid paraffin having a kinematic viscosity of 67.65 mm$^2$/s (40° C.) and an average molecular weight of 483. The results are also shown in Table 3. In Table 3, ○$_{(1)}$ indicates that the composition was stable for one week after standing still, but was separated in about one month.

Evaluation of Applicability to Toothbrush

The applicability of the compositions shown in Table 3 to toothbrushes was evaluated. The obtained compositions were each placed in a tube with a tube diameter φ of about 22 mm and a discharge port diameter φ of about 7 mm, extruded from the tube in an amount roughly corresponding to the length of the long side of the implanted area of GUM Dental Brush #211 (handle material: PET, bristle material: nylon, bristle harness: medium, bristle length: about 10 mm, implanted area size: about 22 mm×about 9 mm), and placed on the horizontally fixed GUM Dental Brush #211. After standing still, the tire until the composition on the brush penetrated between the filaments and completely dripped (retention time) was measured. Further, GUM Dental Brush #211 was soaked in water and pulled from the water while leaving water naturally retained between the filaments (water was retained up to about half the height of the filaments). Using the toothbrush in this state, the retention time when using a wet toothbrush was similarly measured. The results are also shown in Table 3.

The evaluation criteria for the applicability to toothbrushes are as follows. In general, when using a composition placed in a tube by putting it on a toothbrush, as in the present invention, the composition is delivered into the oral cavity from the tube in a relatively short time after being placed on the toothbrush. Therefore, if the composition is retained on the wet toothbrush, from which the composition is more likely to fall, for 10 seconds or longer, it is suitable as a toothbrush composition. It is not suitable that the retention time is less than 10 seconds, because the composition drips before the toothbrush is delivered into the oral cavity, making it difficult to apply a sufficient amount of the composition into the oral cavity.

○: The retention time in the dry state was 10 seconds or longer, and the retention time in the wet state was 10 seconds or longer.

Δ: The retention time in the dry state was 10 seconds or longer, and the retention time in the wet state was less than 10 seconds.

x: The retention time in the dry state was less than 10 seconds.

Evaluation of Applicability to Interdental Brush

The applicability of the compositions shown in Table 3 to interdental brushes was evaluated. The obtained compositions were each placed in a tube with a tube diameter φ of about 16 mm and a discharge port diameter φ of about 1 mm, extruded from the tube in an amount roughly corresponding to the length of the brush of GUM Interdental Brush L Shape (handle: polyethylene, bristles: nylon, wire: stainless steel, size SSS (1): brush length: 10 mm, brush tip diameter: 2 mm, brush rear end diameter: 2.1 nm, minimum passing diameter: at most 0.8 mmφ), and placed on the GUM Interdental Brush L Shape fixed horizontally or with the interdental insertion part of the interdental brush tilted at an angle of 45° with the tip down. After standing still, the time until the composition on the brush penetrated between the filaments and completely dripped (retention time) was measured. Further, GUM Interdental Brush L Shape was soaked in water and pulled from the water while leaving water naturally retained between the filaments. Using the interdental brush in this state, the retention time when using a wet interdental brush was similarly measured. The results are shown in Table 3.

The evaluation criteria for the retention time are as follows. In general, when using a composition placed in a tube by putting it on an interdental brush, as in the present invention, the composition is delivered into the oral cavity from the tube in a relatively short time after being placed on the interdental brush. Therefore, if the composition is retained on the wet interdental brush, from which the composition is more likely to fall, for 20 seconds or longer, it is suitable as an interdental brush composition. It is not suitable that the retention time is less than 20 seconds, because the composition drips before the interdental brush is delivered into the oral cavity, making it difficult to apply a sufficient amount of the composition into the oral cavity.

○: The retention time was 20 seconds or longer.

x: The retention time was less than 20 seconds.

In the dry and horizontal state, all of the compositions did not drip for 120 seconds or longer and were retained on the interdental brushes.

Further, the deliverability of each composition between teeth was examined by inserting GUM Interdental Brush L Shape (size: SSS (1)), on which the composition was put in an amount roughly corresponding to the length of the brush, into a polyethylene cylinder (inner diameter φ: about 1.5 mm), and observing the behavior of the composition. The evaluation criteria for the interdental deliverability are as follows.

○: The composition was delivered into the polyethylene cylinder.

Δ: The composition was on the brush and was retained at the inlet of the polyethylene cylinder. After several insertions, some of the composition entered the polyethylene cylinder.

x: The composition did not enter the inlet of the polyethylene cylinder. The composition fell from the brush.

In addition, the extrudability of each composition from a tube filled with the composition was examined. The evaluation criteria for the extrudability are as follows.

○: The composition could be easily extruded from the tube.

Δ: A little force was required for extrusion.

x: The composition could not be extruded.

As a comprehensive evaluation of the applicability to interdental brushes, those that were evaluated as ○ for all of the retention time, interdental deliverability, and extrudability were regarded as ○, those that were evaluated as G for at least one were regarded as Δ, and those that were evaluated as x for at least one were regarded as x.

TABLE 3

| Example | Polyhydric alcohol | Surfactant | HLB | Hydrocarbon α | B:C:A | B/A | Possibility of preparation | 1 W Stability | Retention time on toothbrush (seconds) Dry state | Wet state | Evaluation (for toothbrush) | Retention time on interdental brush (seconds) Dry state tilted (45°) Result | Evaluation | Wet state horizontal Result | Evaluation | Wet state tilted (45°) Result | Evaluation | Interdental delivery | Extrusion | Evaluation (for interdental brush) |
|---|---|---|---|---|---|---|---|---|---|---|---|---|---|---|---|---|---|---|---|---|
| Example 3-1 | Glycerol | Polyglyceryl-10 stearate | 17.5 | Light liquid paraffin | 35:5:60 | 0.583 | ○ | ○ | 43 | 50 | ○ | >120 | ○ | — | — | >120 | ○ | ○ | ○ | ○ |
| Example 3-2 | Glycerol | Polyglyceryl-10 caprate | 17.3 | Light liquid paraffin | 15:5:80 | 0.188 | ○ | ○ | >120 | >120 | ○ | >120 | ○ | — | — | >120 | ○ | △ | △ | △ |
| Example 3-3 | Glycerol | Polyglyceryl-10 caprate | 17.3 | Light liquid paraffin | 35:5:60 | 0.583 | ○ | ○ | >120 | 27 | ○ | >120 | ○ | >120 | ○ | 65 | ○ | ○ | ○ | ○ |
| Example 3-4 | Glycerol | Polyglyceryl-10 caprate | 17.3 | Light liquid paraffin | 55:5:40 | 1.375 | ○ | ○ | 11 | 3 | △ | >120 | ○ | — | — | 6 | X | ○ | ○ | X |
| Example 3-5 | Glycerol | Polyglyceryl-10 laurate | 17.1 | Light liquid paraffin | 15:5:80 | 0.188 | ○ | ○ | >120 | >120 | ○ | >120 | ○ | >120 | ○ | >120 | ○ | △ | △ | △ |
| Example 3-6 | Glycerol | Polyglyceryl-10 laurate | 17.1 | Light liquid paraffin | 35:5:60 | 0.583 | ○ | ○ | 25 | 56 | ○ | >120 | ○ | >120 | ○ | >120 | ○ | ○ | ○ | ○ |
| Example 3-7 | Glycerol | Polyglyceryl-10 laurate | 17.1 | Light liquid paraffin | 35:5:60 | 0.583 | ○ | ○ | 57 | 50 | ○ | >120 | ○ | >120 | ○ | >120 | ○ | ○ | ○ | ○ |
| Example 3-8 | Glycerol | Polyglyceryl-10 laurate | 17.1 | Light liquid paraffin | 36.25:2.5:61.25 | 0.592 | ○ | ○ | >120 | 29 | ○ | >120 | ○ | >120 | ○ | >120 | ○ | ○ | ○ | ○ |
| Example 3-9 | Glycerol | Polyglyceryl-10 laurate | 17.1 | Light liquid paraffin | 37:1:62 | 0.597 | ○ | ○ | 51 | 20 | ○ | >120 | ○ | >120 | ○ | 38 | ○ | ○ | ○ | ○ |
| Example 3-10 | Glycerol | Polyglyceryl-10 laurate | 17.1 | Light liquid paraffin | 37.25:0.5:62.25 | 0.598 | ○ | ○ | 79 | 30 | ○ | >120 | ○ | >120 | ○ | 34 | ○ | ○ | ○ | ○ |
| Example 3-11 | Glycerol | Polyglyceryl-10 laurate | 17.1 | Light liquid paraffin | 40:5:55 | 0.727 | ○ | ○ | 20 | 19 | ○ | >120 | ○ | >120 | ○ | >120 | ○ | ○ | ○ | ○ |
| Example 3-12 | Glycerol | Polyglyceryl-10 laurate | 17.1 | Light liquid paraffin | 45:5:50 | 0.900 | ○ | ○ | 22 | 5 | △ | >120 | ○ | >120 | ○ | 24 | ○ | ○ | ○ | ○ |
| Example 3-13 | Glycerol | Polyglyceryl-10 laurate | 17.1 | Light liquid paraffin | 55:5:40 | 1.375 | ○ | ○ | 7 | 19 | X | >120 | ○ | >120 | ○ | 5 | X | ○ | ○ | X |
| Example 3-14 | Glycerol | Polyglyceryl-10 laurate | 17.1 | Light liquid paraffin | 60:5:35 | 1.714 | ○ | ○ | 5 | 2 | X | >120 | ○ | >120 | ○ | 4 | X | ○ | ○ | X |
| Example 3-15 | Glycerol | Polyglyceryl-10 laurate | 17.1 | Light liquid paraffin | 70:5:25 | 2.800 | ○ | ○ | 3 | 1 | X | >120 | ○ | 8 | X | 2 | X | ○ | ○ | X |
| Example 3-16 | Glycerol | Polyglyceryl-10 laurate | 17.1 | Light liquid paraffin | 80:5:15 | 5.333 | ○ | ○ | 3 | 1 | X | 70 | ○ | 11 | X | 7 | X | ○ | ○ | X |
| Example 3-17 | Glycerol | Polyglyceryl-10 laurate | 17.1 | Light liquid paraffin | 90:5:5 | 18.000 | ○ | ○ | 2 | 1 | X | 46 | ○ | 5 | X | 1 | X | ○ | ○ | X |
| Example 3-18 | Glycerol | Polyglyceryl-10 myristate | 16.7 | Light liquid paraffin | 35:5:60 | 0.583 | ○ | ○ | 22 | 35 | ○ | >120 | ○ | — | — | >120 | ○ | ○ | ○ | ○ |
| Example 3-19 | Glycerol | Polyglyceryl-10 oleate | 15.9 | Light liquid paraffin | 35:5:60 | 0.583 | ○ | ○ | 28 | 47 | ○ | >120 | ○ | — | — | >120 | ○ | ○ | ○ | ○ |
| Example 3-20 | Glycerol | Polyglyceryl-10 dimyristate | 12.3 | Light liquid paraffin | 15:5:80 | 0.186 | ○ | ○ | 58 | 65 | ○ | >120 | ○ | >120 | ○ | >120 | ○ | ○ | ○ | ○ |
| Example 3-21 | Glycerol | Polyglyceryl-10 dimyristate | 12.3 | Light liquid paraffin | 35:5:60 | 0.583 | ○ | ○ | 25 | 42 | ○ | >120 | ○ | >120 | ○ | >120 | ○ | ○ | ○ | ○ |

TABLE 3-continued

| | Poly-hydric alcohol | Surfactant | HLB | Hydrocarbon | B:C:A | B/A | Possibility of preparation | 1 W Stability | Retention time on toothbrush (seconds) | | Evaluation (for toothbrush) | Retention time on interdental brush (seconds) | | | | | | | Evaluation (for interdental brush) |
|---|---|---|---|---|---|---|---|---|---|---|---|---|---|---|---|---|---|---|---|
| | | | | | | | | | Dry state | Wet state | | Dry state tilted (45°) | | Wet state horizontal | | Wet state tilted (45°) | | Interdental delivery | Extrusion | |
| | | | | | | | | | | | | Result | Evaluation | Result | Evaluation | Result | Evaluation | | | |
| Example 3-22 | Glycerol | Polyglyceryl-10 distearate | 11.1 | Light liquid paraffin | 35:5:60 | 0.583 | ○ | ○ | >120 | >120 | ○ | >120 | ○ | >120 | ○ | >120 | ○ | △ | △ | △ |
| Example 3-23 | Glycerol | Polyglyceryl-10 distearate | 11.1 | Light liquid paraffin | 65:5:30 | 2.167 | ○ | ○ | >120 | >120 | ○ | >120 | ○ | — | — | >120 | ○ | △ | △ | △ |
| Example 3-24 | Glycerol | Polyglyceryl-10 distearate | 11.1 | Light liquid paraffin | 80:5:15 | 5.333 | ○ | ○ | 5 | 2 | X | 32 | ○ | — | — | 10 | X | ○ | ○ | X |
| Example 3-25 | Glycerol | Polyglyceryl-10 disostearate | 11.1 | Light liquid paraffin | 35:5:60 | 0.583 | ○ | ○ | >120 | >120 | ○ | >120 | ○ | >120 | ○ | >120 | ○ | △ | ○ | △ |
| Example 3-26 | Glycerol | Polyglyceryl-10 disostearate | 11.1 | Light liquid paraffin | 65:5:30 | 2.167 | ○ | ○ | 28 | 32 | ○ | — | — | — | — | — | — | — | — | — |
| Example 3-27 | Glycerol | Polyglyceryl-10 trilaurate | 10.4 | Light liquid paraffin | 65:5:30 | 2.167 | ○ | ○ | 9 | 7 | X | 96 | ○ | >120 | ○ | 5 | X | ○ | ○ | X |
| Example 3-28 | Glycerol | Polyglyceryl-10 trilaurate | 10.4 | Light liquid paraffin | 85:5:10 | 8.500 | ○ | ○ | 4 | 2 | X | 89 | ○ | 10 | X | 3 | X | ○ | ○ | X |
| Example 3-20 | Glycerol | Polyglyceryl-5 trimyristate | 7.8 | Light liquid paraffin | 35:5:60 | 0.583 | ○ | ○(1) | — | — | — | — | — | — | — | — | — | — | — | — |

It was revealed that the compositions shown in the Examples were not phase-separated, and stably maintained their emulsion state after another week. Further, it was revealed that some of the compositions shown in the Examples were suitable for use with toothbrushes (Examples 3-1 to 3-3, 3-5 to 3-11, 3-18 to 3-23, 3-25, and 3-26). It was also revealed that some of the compositions shown in the Examples were suitable for use with interdental brushes (Examples 3-1, 3-3, 3-6 to 3-12, and 3-18 to 3-21).

Preparation 3 of Oral Composition

According to the formulations shown in Tables 4 and 5 (the numerical values indicate mass %), in addition to glycerol and light liquid paraffin, various surfactants were added to prepare oral compositions, and their stability was evaluated in the same manner as described above. The alkyl glycoside used in Table 5 was Plantacare 1200UP (BASF), and more specifically an aqueous solution of polyglycoside with a $C_{12-16}$ alkyl alcohol. The water content was about 47 to 50%. The results are shown in Tables 4 and 5. The compositions shown in Table 5 were evaluated for their applicability to toothbrushes in the same manner as described above. The results are also shown in Table 5.

Preparation 4 of Oral Composition

According to the formulations shown in Tables 6 to 8 (the numerical values indicate mass %), in addition to various polyhydric alcohols and light liquid paraffin, various surfactants were added to prepare oral compositions, and their stability was evaluated in the same manner as described above. The results are also shown in Tables 6 to 8.

TABLE 6

| Substance name | HLB | Comparative Example 6-1 | Example 6-1 | Example 6-2 |
|---|---|---|---|---|
| Propylene glycol | — | 35 | 35 | 35 |
| Light liquid paraffin | — | 60 | 60 | 60 |
| POE (15) oleyl ether | 16.0 | 5 | | |
| PEG-100 hydrogenated castor oil | 16.5 | | 5 | |
| PEG-5 hydrogenated castor oil isostearate | 12.0 | | | 5 |
| Possibility of preparation | | ○ | ○ | ○ |
| 1 W stability | | x | ○ | ○ |

TABLE 4

Examination of surfactants other than polyglycerol fatty acid esters for glycerol

| Substance name | HLB | Comparative Example 4-1 | Comparative Example 4-2 | Comparative Example 4-3 | Comparative Example 4-4 | Comparative Example 4-5 | Comparative Example 4-6 | Comparative Example 4-7 | Comparative Example 4-8 |
|---|---|---|---|---|---|---|---|---|---|
| Glycerol | — | 5 | 5 | 35 | 5 | 5 | 35 | 35 | 35 |
| Light liquid paraffin | — | 90 | 90 | 60 | 90 | 90 | 60 | 60 | 60 |
| POE(5.5) cetyl ether | 10.5 | 5 | | | | | | | |
| POE(15) cetyl ether | 15.5 | | 5 | 5 | | | | | |
| PEG-50 hydrogenated castor oil | 13.5 | | | | 5 | | | | |
| PEG-100 hydrogenated castor oil | 16.5 | | | | | 5 | 5 | | |
| PEG-5 hydrogenated castor oil isostearate | 12.0 | | | | | | | 5 | |
| POE sorbitan monooleate | 15.0 | | | | | | | | 5 |
| Possibility of preparation | | X | X | X | X | X | X | X | X |
| 1 W stability | | X | X | X | X | X | X | X | X |
| B/A | | 0.056 | 0.056 | 0.583 | 0.056 | 0.056 | 0.583 | 0.583 | 0.583 |

TABLE 5

Change in the mixing ratio of glycerol and paraffin when using alkyl glucoside

| Substance name | HLB | | Example 5-1 | Example 5-2 | Example 5-3 | Example 5-4 | Example 5-5 | Example 5-6 |
|---|---|---|---|---|---|---|---|---|
| Glycerol | — | | 15 | 35 | 55 | 35 | 37 | 36.25 |
| Light liquid paraffin | — | | 80 | 60 | 40 | 60 | 62 | 61.25 |
| Alkyl glucoside | 16.1 | | 5 | 5 | 5 | 5 | 1 | 2.5 |
| Possibility of preparation | | | ○ | ○ | ○ | ○ | ○ | ○ |
| 1 W stability | | | ○ | ○ | ○ | ○ | ○ | ○ |
| B/A | | | 0.188 | 0.583 | 1.375 | 0.583 | 0.597 | 0.592 |
| Retention time on toothbrush (seconds) | Dry state | | >120 | 21 | 5 | — | 27 | — |
| | Wet state | | >120 | 12 | 4 | — | 10 | — |
| Evaluation (for toothbrush) | | | ○ | ○ | X | — | ○ | — |

It was revealed that the compositions shown in the Examples were not phase-separated, and stably maintained their emulsion state after another week. Further, it was revealed that some of the compositions shown in the Examples shown in Table 5 were suitable for use with toothbrushes (Examples 5-1, 5-2, and 5-5).

TABLE 7

| Substance name | HLB | Example 7-1 | Comparative Example 7-1 | Example 7-2 |
|---|---|---|---|---|
| 1, 3-butylene glycol | — | 35 | 35 | 35 |
| Light liquid paraffin | — | 60 | 60 | 60 |
| POE (15) oleyl ether | 16.0 | 5 | | |

TABLE 7-continued

| Substance name | HLB | Example 7-1 | Comparative Example 7-1 | Example 7-2 |
|---|---|---|---|---|
| PEG-100 hydrogenated castor oil | 16.5 | | 5 | |
| PEG-5 hydrogenated castor oil isostearate | 12.0 | | | 5 |
| Possibility of preparation | | ○ | ○ | ○ |
| 1 W stability | | ○ | x | ○ |

TABLE 8

| Substance name | HLB | Comparative Example 8-1 | Comparative Example 8-2 | Comparative Example 8-3 | Example 8-1 |
|---|---|---|---|---|---|
| Polyethylene glycol 400 | — | 35 | 35 | 35 | 35 |
| Light liquid paraffin | — | 60 | 60 | 60 | 60 |
| Polyglyceryl-10 laurate | 17.1 | 5 | | | |
| POE (15) oleyl ether | 16.0 | | 5 | | |
| PEG-100 hydrogenated castor oil | 16.5 | | | 5 | |
| PEG-5 hydrogenated castor oil isostearate | 12.0 | | | | 5 |
| Possibility of preparation | | x | ○ | x | ○ |
| 1 W stability | | x | x | x | ○ |

It was revealed that the compositions shown in the Examples were not phase-separated, and stably maintained their emulsion state after another week.

The formulation examples of the oral composition of the present invention are shown below. The amount (%) of each formulation example indicates mass %. A composition of glycerol, polyglyceryl-10 laurate, and light liquid paraffin (35:5:60) was used as the base. The following formulations were stable with no oil separation even after standing still at room temperature for one week.

TABLE 9

| Toothpaste | |
|---|---|
| Component name | Proportion (%) |
| Silicic anhydride | 30 |
| Hydroxyethyl cellulose | 1 |
| Sodium polyacrylate | 1 |
| Coconut oil fatty acid amide propyl betaine liquid | 2 |
| Cetylpyridinium chloride hydrate | 1 |
| Pyridoxine hydrochloride | 0.02 |
| β-glycyrrhetinic acid | 0.2 |
| Saccharine sodium | 0.3 |
| Mixed dye L (diisostearyl malate: 70%, legal dye: 30%) | 0.01 |
| Fragrance | 0.1 |
| Base | 64.37 |

TABLE 10

| Toothpaste | |
|---|---|
| Component name | Proportion (%) |
| Silicic anhydride | 20 |
| Precipitated calcium carbonate | 10 |

TABLE 10-continued

| Toothpaste | |
|---|---|
| Component name | Proportion (%) |
| Sodium carboxymethylcellulose | 1 |
| Sodium alginate | 1 |
| Sodium lauryl sulfate | 1 |
| Sodium monofluorophosphate | 1.14 |
| Isopropyl methyl phenol | 0.1 |
| Tocopherol acetate ester | 1 |
| Stevia extract | 0.5 |
| Sodium citrate | 1 |
| Mica titanium | 0.1 |
| Fragrance | 0.1 |
| Base | 63.06 |

TABLE 11

| Gel | |
|---|---|
| Component name | Proportion (%) |
| Sodium carboxymethylcellulose | 1 |
| Xanthane gum | 1 |
| Sodium lauryl sulfate | 1 |
| Sodium fluoride | 0.32 |
| Sodium lauroyl sarcosinate | 0.5 |
| Dipotassium glycyrrhizinate | 0.05 |
| Zinc oxide | 3 |
| Reduced palatinose | 10 |
| Xylitol | 10 |
| p-Hydroxybenzoate ester | 0.3 |
| Sodium hydrogen phosphate | 1 |
| Blue No. 1, its aluminum lake, its barium lake, and its zirconium lake | 0.01 |
| Fragrance | 0.1 |
| Hesperidin | 1 |
| Base | 70.72 |

TABLE 12

| Toothpaste | |
|---|---|
| Component name | Proportion (%) |
| Silicic anhydride | 10 |
| Xanthane gum | 1 |
| Sodium alginate | 1 |
| Sodium fluoride | 0.32 |
| Cetylpyridinium chloride hydrate | 1 |
| Lysozyme hydrochloride | 4 |
| Stevia extract | 0.5 |
| Sodium hydrogen phosphate | 1 |
| Titanium oxide | 2 |
| Fragrance | 1 |
| Base | 78.18 |

TABLE 13

| Gel | |
|---|---|
| Component name | Proportion (%) |
| Triclosan | 0.02 |
| Allantoin | 0.5 |
| Glucosyl trehalose/hydrogenated starch decomposition product mixed solution | 15 |
| Sodium hydrogen phosphate | 1 |
| 1-Menthol | 0.5 |
| Base | 82.98 |

27

TABLE 14

Dermatological paste

| Component name | Proportion (%) |
|---|---|
| Hydroxyapatite | 10 |
| Light silicic anhydride | 5 |
| Sodium monofluorophosphate | 1.14 |
| Isopropyl methyl phenol | 0.1 |
| Tocopherol acetate ester | 1 |
| Aluminum lactate | 2 |
| Saccharine sodium | 0.3 |
| p-Hydroxybenzoate ester | 0.3 |
| Titanium oxide | 2 |
| Fragrance | 0.1 |
| Base | 78.06 |

TABLE 15

Toothpaste

| Component name | Proportion (%) |
|---|---|
| Heavy calcium carbonate | 10 |
| Sodium carboxymethylcellulose | 1 |
| Xanthane gum | 1 |
| Tocopherol acetate ester | 1 |
| Angelica root liquid extract | 0.01 |
| Potassium nitrate | 5 |
| Sodium chloride | 15 |
| Sodium benzoate | 0.3 |
| Titanium oxide | 2 |
| Fragrance | 1 |
| Base | 63.69 |

TABLE 16

Toothpaste

| Component name | Proportion (%) |
|---|---|
| Heavy calcium carbonate | 20 |
| Calcium hydrogen phosphate for tooth brushing | 10 |
| Sodium carboxymethylcellulose | 1 |
| Xanthane gum | 1 |
| Sodium lauryl sulfate | 1 |
| Sodium monofluorophosphate | 1.14 |
| Tocopherol acetate ester | 1 |
| Stevia extract | 0.5 |
| Sodium benzoate | 0.3 |
| Titanium oxide | 2 |
| Fragrance | 1 |
| Base | 61.06 |

TABLE 17

Ointment

| Component name | Proportion (%) |
|---|---|
| Hydroxyethyl cellulose | 1 |
| Sodium fluoride | 0.32 |
| Chlorhexidine hydrochloride | 0.05 |
| Potassium nitrate | 5 |
| Saccharine sodium | 0.3 |
| Blue No. 1, its aluminum lake, its barium lake, and its zirconium lake | 0.01 |
| Fragrance | 1 |
| Base | 92.32 |

28

The invention claimed is:

1. An oral composition comprising a hydrocarbon oil, a polyhydric alcohol, and a surfactant, the oral composition comprising:
   (i) propanediol, and a polyoxyethylene hardened castor oil,
   (ii) butylene glycol, and a polyoxyethylene alkyl ether and/or a polyoxyethylene hardened castor oil fatty acid ester, or
   (iii) polyethylene glycol and a polyoxyethylene hardened castor oil fatty acid ester,
   wherein the oral composition has a water content of 5 mass % or less, and
   wherein a content mass ratio of the polyhydric alcohol and the hydrocarbon oil measured as (mass of polyhydric alcohol/mass of hydrocarbon oil) is 0.1 to 1.1.

2. The oral composition according to claim 1, which is a non-aqueous composition.

3. The oral composition according to claim 1, which is not phase-separated after being allowed to stand at 25° C. for one week after preparation.

4. The oral composition according to claim 1, wherein the hydrocarbon oil is paraffin.

5. The oral composition according to claim 1, which is used with a toothbrush composition.

6. The oral composition according to claim 1, which comprises
   (i) propanediol and a polyoxyethylene hardened castor oil.

7. The oral composition according to claim 1, which comprises
   (ii) butylene glycol, and a polyoxyethylene alkyl ether and/or a polyoxyethylene hardened castor oil fatty acid ester.

8. A composition that is a carrier for an oral composition and comprises a hydrocarbon oil, a polyhydric alcohol, and a surfactant, the composition comprising:
   (i) propanediol, and a polyoxyethylene hardened castor oil,
   (ii) butylene glycol, and a polyoxyethylene alkyl ether and/or a polyoxyethylene hardened castor oil fatty acid ester, or
   (iii) polyethylene glycol and a polyoxyethylene hardened castor oil fatty acid ester,
   wherein the composition has a water content of 5 mass % or less, and
   wherein a content mass ratio of the polyhydric alcohol and the hydrocarbon oil measured as (mass of polyhydric alcohol/mass of hydrocarbon oil) is 0.1 to 1.1.

9. The composition according to claim 8, which comprises
   (i) propanediol and a polyoxyethylene hardened castor oil.

10. The composition according to claim 8, which comprises
   (ii) butylene glycol, and a polyoxyethylene alkyl ether and/or a polyoxyethylene hardened castor oil fatty acid ester.

11. The composition according to claim 8, which is a non-aqueous composition.

12. The composition according to claim 8, wherein the hydrocarbon oil is paraffin.

13. The composition according to claim 8, which is used with a toothbrush composition.

14. An oral composition comprising a hydrocarbon oil, a polyhydric alcohol, and a surfactant, the oral composition comprising:

(a) propanediol and a polyoxyethylene hardened castor oil fatty acid ester, (b) propanediol, a polyoxyethylene hardened castor oil, and a polyoxyethylene hardened castor oil fatty acid ester, or (c) polyethylene glycol and a polyoxyethylene hardened castor oil fatty acid ester, wherein the oral composition has a water content of 5 mass % or less, and wherein a content mass ratio of the polyhydric alcohol and the hydrocarbon oil measured as (mass of polyhydric alcohol/mass of hydrocarbon oil) is 0.1 to 1.1.

15. The oral composition according to claim 14, which comprises (a) propanediol and a polyoxyethylene hardened castor oil fatty acid ester.

16. The oral composition according to claim 14, which comprises (b) propanediol, a polyoxyethylene hardened castor oil, and a polyoxyethylene hardened castor oil fatty acid ester.

17. The oral composition according to claim 14, which comprises (c) polyethylene glycol and a polyoxyethylene hardened castor oil fatty acid ester.

18. The oral composition according to claim 14, which is a non-aqueous composition.

19. The oral composition according to claim 14, wherein the hydrocarbon oil is paraffin.

20. The oral composition according to claim 14, which is used with a toothbrush composition.

* * * * *